United States Patent
McQuilkin

(10) Patent No.: US 7,340,293 B2
(45) Date of Patent: Mar. 4, 2008

(54) METHODS AND APPARATUS FOR A REMOTE, NONINVASIVE TECHNIQUE TO DETECT CORE BODY TEMPERATURE IN A SUBJECT VIA THERMAL IMAGING

(76) Inventor: Gary L. McQuilkin, 14860 46th Ave. North, Plymouth, MN (US) 55446

( * ) Notice: Subject to any disclaimer, the term of this patent is extended or adjusted under 35 U.S.C. 154(b) by 0 days.

(21) Appl. No.: 10/854,574

(22) Filed: May 25, 2004

(65) Prior Publication Data

US 2004/0254472 A1    Dec. 16, 2004

Related U.S. Application Data

(60) Provisional application No. 60/471,747, filed on May 27, 2003.

(51) Int. Cl.
*A61B 5/01* (2006.01)
(52) U.S. Cl. .................... 600/474; 600/549; 374/121; 374/128; 374/129; 374/133
(58) Field of Classification Search ................ 600/474, 600/549; 374/121, 126, 128, 129, 133
See application file for complete search history.

(56) References Cited

U.S. PATENT DOCUMENTS

| 4,275,741 | A |   | 6/1981  | Edrich              |
|-----------|---|---|---------|---------------------|
| 4,407,292 | A |   | 10/1983 | Edrich              |
| 4,993,424 | A | * | 2/1991  | Suszynski et al. .......... 600/549 |
| 5,115,815 | A | * | 5/1992  | Hansen ....................... 600/474 |
| 5,293,877 | A |   | 3/1994  | O'Hara et al.       |
| 5,324,937 | A |   | 6/1994  | Chen et al.         |
| 5,386,831 | A | * | 2/1995  | Gluck ......................... 600/474 |
| 5,420,419 | A |   | 5/1995  | Wood                |
| 5,450,053 | A |   | 9/1995  | Wood                |
| 5,675,149 | A |   | 10/1997 | Wood et al.         |
| 5,678,555 | A |   | 10/1997 | O'Connell           |
| 5,874,736 | A |   | 2/1999  | Pompei              |
| 5,893,833 | A |   | 4/1999  | Pompei et al.       |
| 6,045,257 | A |   | 4/2000  | Pompei et al.       |
| 6,056,435 | A | * | 5/2000  | Pompei ..................... 374/133 |
| 6,144,031 | A |   | 11/2000 | Herring et al.      |
| 6,241,384 | B1|   | 6/2001  | Pompei et al.       |

(Continued)

OTHER PUBLICATIONS

Pompei, F. et al., "Arterial Thermometry Via Heat Balance at the Ear," *Physicians Reference Handbook of Temperature*, 1996.

*Primary Examiner*—Ruth S. Smith
(74) *Attorney, Agent, or Firm*—Kagan Binder, PLLC

(57) ABSTRACT

An approach to noninvasively, remotely and accurately detect core body temperature in a warm-blooded subject, human or animal, via thermal imaging. Preferred features such as the use of in-frame temperature references, specific anatomical target regions and a physiological heat transfer model help the present invention to overcome pitfalls inherent with existing thermal imaging techniques applied to physiological screening applications. This invention provides the ability to noninvasively, remotely and rapidly screen for diseases or conditions that are characterized by changes in core body temperature. One human application of this invention is the remote screening for severe acute respiratory syndrome (SARS), since fever is a common, early symptom. Other diseases and conditions that affect the core body temperature of humans or animals may also be noninvasively and remotely detected with this invention.

32 Claims, 8 Drawing Sheets

U.S. PATENT DOCUMENTS

| | | |
|---|---|---|
| 6,300,632 B1 | 10/2001 | Liu et al. |
| 6,402,371 B2 | 6/2002 | Pompei et al. |
| 6,524,239 B1 * | 2/2003 | Reed et al. ................ 600/300 |
| 6,547,744 B1 | 4/2003 | Pompei et al. |
| 6,559,447 B2 | 5/2003 | Wood |
| 6,596,997 B2 | 7/2003 | Kaufman |
| 6,606,115 B1 | 8/2003 | Alicandro et al. |
| 6,631,287 B2 | 10/2003 | Newman et al. |
| 6,709,154 B1 | 3/2004 | Janotte |
| 2002/0143257 A1 * | 10/2002 | Newman et al. ............ 600/474 |
| 2003/0067958 A1 * | 4/2003 | Jang ........................... 374/131 |
| 2003/0142723 A1 * | 7/2003 | Laurence et al. ........... 374/121 |
| 2004/0019269 A1 * | 1/2004 | Schaefer et al. ............ 600/407 |
| 2004/0154550 A1 | 8/2004 | McQuilkin |

* cited by examiner

METHODS AND APPARATUS FOR A REMOTE, NONINVASIVE TECHNIQUE TO DETECT CORE BODY TEMPERATURE IN A SUBJECT VIA THERMAL IMAGING

PRIORITY CLAIM

The present non-provisional, U.S. Patent Application claims priority under 35 USC §119(e) from U.S. Provisional Patent Application having Ser. No. 60/471,747, filed on May 27, 2003, in the name of Gary L. McQuilkin and titled METHODS AND APPARATUS FOR A REMOTE, NONINVASIVE TECHNIQUE TO DETECT OF CORE BODY TEMPERATURE IN A SUBJECT VIA THERMAL IMAGING and wherein said U.S. Provisional Patent Application is commonly owned by the assignee of the present application and wherein the entire contents of said U.S. Provisional Patent Application is incorporated herein by reference.

FIELD OF THE INVENTION

This invention is directed to an approach to noninvasively and remotely detect core body temperature in a warm-blooded subject. More specifically, this invention is directed to an approach to noninvasively and remotely detect core body temperature in a warm-blooded subject, human or animal, via thermal imaging.

BACKGROUND OF THE INVENTION

Many parts of the world are presently threatened by the spread of new, deadly, and contagious diseases, such as severe acute respiratory syndrome (SARS), or the possibility of terrorist attacks with biological weapons. Travelers may spread dangerous microbes intentionally or unintentionally. The screening technologies that detect guns, knives, or explosives are of little value against these new biological hazards. Standard medical diagnostic techniques are time-consuming and unsuited for mass screening at places such as airports, ports of entry, immigration stations, crowded malls, or places of business. The present invention provides the ability to screen the masses for diseases characterized by the presence of a fever or elevation in body temperature.

Extreme temperatures may overcome the thermoregulatory system of the body. Physical exertion under hot humid conditions may result in heat stroke, which is characterized by a dangerous rise in core body temperature. Exposure to extreme cold temperatures may result in hypothermia, which is a dangerous decrease in core body temperature. The present invention provides an approach to remotely and noninvasively monitoring body temperatures during exposure to extreme ambient temperatures so that medical intervention may occur in a timely manner.

Animal diseases such as chronic wasting disease (CWD), mad cow disease, scrapies, and West Nile Virus all exhibit thermoregulatory components. The present invention is valuable as part of a noninvasive and remote screening regimen for these diseases.

According to the Center for Disease Control (CDC), severe acute respiratory syndrome (SARS) is a respiratory illness that has recently been reported in Asia, North America, and Europe. In general, SARS begins with a fever greater than 100.4° F. [>38.0° C.]. Other symptoms may include headache, an overall feeling of discomfort, and body aches. Initially, some people experience mild respiratory symptoms. After 2 to 7 days, SARS patients may develop a dry cough and have difficulty breathing. In 10-20% of cases, the respiratory illness is severe enough to require intubation and mechanical ventilation. The mortality rate is reported to be 20% for those under age 60 and 40% for those over age 60.

SARS appears to be spread by close person-to-person contact. Most cases of SARS have involved people who have cared for a SARS patient or had direct contact with infectious material such as respiratory secretions. SARS may be acquired by a healthy individual if that individual touches the skin of an infected person or objects which are contaminated with infectious droplets and then in turn touches the eye(s), nose or mouth of the healthy individual. This can readily happen when a person, sick with SARS, coughs or sneezes droplets onto themselves, other people or nearby surfaces. SARS may also be spread more broadly through the air or by other ways not yet known.

According to Dr. J. Gerberding, director for the Centers for Disease Control and Prevention, the SARS virus can quickly get out of control. It is necessary to take all steps to detect new cases and isolate them in the hospital or at home until the contagious period has passed. While it is very important to pursue a vaccine, this virus will not likely be eradicated soon.

The criteria presently used to detect new cases and screen subjects for SARS include: an elevated temperature greater than 100.4° F. (38.0° C.), a dry persistent cough, and travel to an area of known SARS presence or exposure to a known SARS patient.

Since an elevated temperature greater than 100.4° F. (38.0° C.) is one of the earliest indicators for SARS, clinicians and government leaders are looking to thermal measurement techniques as screening tools to limit the transmission of the disease and to identify potential SARS subjects via mass screening at public sites such as airports, ports of entry, immigration stations, crowded malls, or places of business. Many levels of government (Federal, State, and local) have the authority to require the isolation of sick persons to protect the general public.

In addition to SARS, many other diseases or conditions have a change in body temperature as an indicator. Additionally, numerous infectious diseases, conditions associated with biological weapons, and heat stroke may be indicated by an increase in body temperature. Hypothermia from exposure or surgery may also be accurately detected by a decrease in body temperature.

Additional examples of diseases for which mass screening may be advantageous include viral agents such as smallpox, Ebola hemorrhagic fever, Lassa fever, Congo fever, viral hemorrhagic fever, Enteric fever, Meningococcal infection, tuberculosis, and smallpox. Bacterial agents such as plague may be detected. Screening for preformed biological toxins such as staphylococcal enterotoxin B, ricin, and T-2 Mycotoxin may also be possible.

A review of current clinical methods for measuring body temperature finds no present method is well-suited for rapidly screening large numbers of people. Body temperature is commonly measured by either oral, rectal, axillary or tympanic methods. Oral temperatures are obtained by placing a clinical thermometer under the tongue for 2-3 minutes with a normal reading of 98.6° F. Rectal temperatures are obtained by placing a thermometer at least 1½ inches (3.75 cm) into the anal canal for 3-5 minutes with a normal reading 0.5 to 1.0° F. above oral temperatures. Axillary temperatures are obtained by placing a thermometer under the armpit while placing the arm tightly against the body with normal temperatures approximately 0.5° F. lower than oral temperatures. Eardrum or tympanic temperatures may be obtained via an infrared device placed into the ear canal with normal temperatures similar to oral temperature values. Each of these standard measurement methods requires several minutes to obtain the measurement and/or close personal contact with the patient—significant disadvantages for mass screening of a contagious disease. Additionally, the above methods require the disposal of large volumes of contaminated thermometer sheaths or ear canal adapters.

Since current clinical methods for measuring body temperature are not well-suited for SARS screening, clinicians, scientists, and entrepreneurs are attempting to use thermal imaging for this purpose. In basic principle, thermal imaging can thermally scan an individual patient or large numbers of people rapidly and remotely. Thermal imaging technology can obtain thermal images at a video rate (30 images per second) compared to current clinical methods that take minutes for each measurement. Thermal imaging can also obtain the images from a distance of several feet to hundreds of feet depending upon the optical system employed, thus overcoming the disadvantage of close contact with potentially contagious patients. However, the direct application of thermal imaging, in its present state, to measure body temperature has serious shortcomings.

While it is desired to obtain measurements of core body temperature for each patient via thermal imaging techniques, present thermal imaging techniques provide only a measurement of surface or skin temperatures. In general, skin temperature varies with ambient temperature, anatomical site and circulatory perfusion. For a constant oral temperature of 98.6° F. the skin temperatures may be 96.0, 91.0, and 86.5° F., for ambient temperatures of 90, 70, and 55° F., respectively. The skin temperatures of various anatomical sites such as the nose, ears, cheeks, forehead and eyes may vary by 10-15° F. Cardiovascular dynamics and even psychological variables may also change skin temperatures in such sites as the cheeks, ears or nose.

In addition to the variability of absolute skin temperatures, many of the thermal imaging systems in use today have absolute thermal tolerances that are inappropriate for body temperature measurements. Many thermal imaging systems have tolerances of +/−2° C. (+/−3.6° F.). With such tolerances, a skin temperature of 91.0° F. (ambient temperature, 70° F.), which corresponds to an oral temperature of 98.6° F., could be recorded as a skin temperature of 87.4° F. to 94.6° F. and still remain within the camera tolerances.

Although present thermal imaging technology can provide rapid and remote acquisition of skin temperatures, these skin temperatures cannot provide temperature measurements that are accurately correlated to core body temperatures, regardless of the accuracy of the temperature measurement. Without accurate linkage to core body temperatures, the readings have little clinical significance. The value is limited to the identification of individuals that have higher (or lower) skin temperatures relative to a group of individuals experiencing similar ambient, emotional and exertion conditions at that particular time and location.

Additionally, some manufacturers of thermal imaging systems have added image averaging techniques, alarms for the detection of persons with elevated skin temperatures, color highlighted images for alarm conditions and other features which fall into the category of 'bells and whistles'. While these features might prove useful when based on accurate core body temperature measurements, they become nuisance alarms when based upon inaccurate or relative indications.

There exists a need to rapidly, remotely and accurately measure core body temperature. This desired technique should exhibit the rapid and remote screening characteristics of present thermal imaging technology coupled with the accurate measurements of body temperature exhibited by present clinical techniques. With such a combination, large numbers of people could be accurately screened for elevated core body temperatures and properly treated or isolated. The present invention addresses these goals.

SUMMARY OF THE INVENTION

The present invention provides an approach for rapidly, noninvasively, and remotely obtaining an accurate measurement of core body temperature. This invention is directed to an approach to noninvasively and remotely detect core body temperature in a warm-blooded subject, human or animal, via thermal imaging. The present invention uses thermal imaging technology to acquire accurate skin temperature data from physiologically preferred sites and then converts these data to clinically significant, core body temperatures via a thermal model and algorithm.

This invention provides the ability to noninvasively, remotely and accurately screen for diseases or other conditions that are characterized by changes in core body temperature. For instance, one representative application of this invention is the remote screening for severe acute respiratory syndrome (SARS), since it commonly exhibits a fever as an early symptom.

While SARS has been mentioned thus far, the present invention is useful as a screening tool for many diseases or conditions that have a change in core body temperature as an indicator. Other diseases and conditions that affect the core body temperature of humans and animals also may be noninvasively and remotely detected with this invention. Numerous other infectious diseases and conditions induced by biological weapons may be detected by an increase in body temperature. Hypothermia from exposure or surgery may also be accurately detected by a decrease in core body temperature. Additional examples of diseases for which mass screening may be advantageous include viral agents such as smallpox, Ebola hemorrhagic fever, Lassa fever, Congo fever, viral hemorrhagic fever, Enteric fever, Meningococcal infection, tuberculosis, and smallpox. Bacterial agents such as plague may be detected. Screening for preformed biological toxins such as staphylococcal enterotoxin B, ricin, and T-2 Mycotoxin may also be possible.

The present invention is also useful for screening persons for heat stroke, such as under conditions of high ambient temperatures. Diverse groups of individuals such as athletes, military personnel, state fair goers or farm workers are candidates for heat stroke monitoring via the present invention.

Animal and veterinary needs also exist for the present invention. Presently screening animals for fever or hypothermia requires direct, invasive measurement techniques. The ability to remotely and noninvasively screen animals for changes in core body temperature is safer for the animal since capture or tranquillizers are not required. There is also additional safety, convenience and economy afforded the veterinarian or manager by replacing a direct contact or capture event with a noninvasive, remote monitoring procedure.

The use of thermal imaging techniques to derive temperature information has numerous practical advantages. As one example, the thermal imaging data may be processed via digital signal processing technology in real time. Thus, an immediate diagnosis is available so that medical personnel may treat or isolate subjects immediately.

As another example, the thermal imaging equipment operates remotely at a distance limited only by the optics of the system. This distance, anywhere from 2 feet to hundreds of feet, provides safety for the medical personnel in the event that the disease or condition, such as SARS, is contagious and dangerous.

The accuracy of the temperature data may be improved by using one or more data gathering and management techniques either singly or in combination. For example, improved accuracy may be obtained by using in-frame temperature reference(s), out-of-frame temperature reference(s), or through the use of a thermal camera having high temperature accuracy. In preferred embodiments, a preferred triple temperature reference in an image frame provides first and second bracketed reference temperatures around the anticipated skin temperature and then a third ambient temperature reference. Accuracy also may be improved by identifying physiologically preferred measurement sites from which to sample temperature and then derive core body temperature. Such preferred sites include the regions around the eyes and the forehead, that exhibit more thermal stability than more peripheral sites such as the ears, cheeks or nose. Desirably, thermal image resolution allows a sufficient number of pixels to fall on the anatomical target(s) of interest.

The use of in-frame references, specific anatomical target regions and a physiological heat transfer model enables the present invention to overcome pitfalls inherent with existing thermal imaging techniques applied to physiological screening applications. Additionally, the present invention provides facile methodologies by which to derive core body temperature from the thermal image data. As one example, the present invention provides a preferred thermal model that compensates the computed core body temperature for changes in parameters such as ambient temperature, skin temperature and humidity on a frame-by-frame basis. A calibration strategy to compute core body temperatures that tracks oral, axillary, rectal or tympanic temperatures may also be used. Image processing strategies also may be used such that the thermal data resolution may be increased, thermal edges may be corrected (if necessary), lowpass filters may be engaged to reduce image noise, and area averaging (mean, median, weighted, etc.) may be employed to optimize measurement stability.

In one aspect, the present invention relates to a thermal imaging system that provides core body temperature information of a subject. The system includes a thermal imaging device that acquires thermal image data of the subject when the subject is within a field of view of the device. The system also includes program instructions that derive core body temperature information for the subject using the thermal image data.

In another aspect, the present invention relates to a method of remotely determining a core body temperature of a subject. Thermal image data is acquired for at least a portion of the subject. The core body temperature of the subject is derived using the thermal image data.

In another aspect, the present invention relates to a method of screening for SARS. Thermal image data of at least a portion of a subject is acquired. A core body temperature of the subject is determined based on the thermal image data. The determined core body temperature is used to assess whether the subject may have SARS.

In another aspect, the present invention relates to a method of screening for a health condition. A thermal image of at least a portion of a subject is acquired. A core body temperature of the subject is determined based on the thermal image data. The determined core body temperature is used to assess whether the subject may have a health condition. Health conditions include SARS, smallpox, health conditions associated with bio-terrorism, heat-stroke, hypothermia, chronic wasting disease, mad cow disease, scrapies, West Nile virus, and the like.

In another aspect, the present invention relates to a method of determining a core body temperature of a subject. Thermal image data of an eye region of the target subject is acquired. A core body temperature of the subject is determined based on thermal image data associated with the eye region.

In another aspect, the present invention relates to a method of determining a core body temperature of a subject. Thermal image data of a forehead region of the target subject is acquired. A core body temperature of the subject is determined based on thermal image data associated with the forehead region.

In another aspect, the present invention relates to a method of screening a target body for an abnormal core body temperature. At least one surface temperature of the target body is derived remotely. A core body temperature of the target is determined from the at least one surface temperature of the target body.

In another aspect, the present invention relates to a method of determining a core body temperature of a target body. Thermal image data of a subject and a surface associated with an ambient temperature are simultaneously acquired. The core body temperature of the target body is derived from the simultaneously acquired surface and ambient temperature thermal image data.

In another aspect, the present invention relates to a method of detecting a core body temperature of an animal. A core body temperature of the animal is determined using thermal image data. A health condition of the animal is evaluated based on the determined core body temperature.

BRIEF DESCRIPTION OF THE DRAWINGS

The understanding of the above mentioned and other advantages of the present invention, and the manner of attaining them, and the invention itself can be facilitated by reference to the following description of the exemplary embodiments of the invention taken in conjunction with the accompanying drawings, wherein.

DETAILED DESCRIPTION

Figure 1:
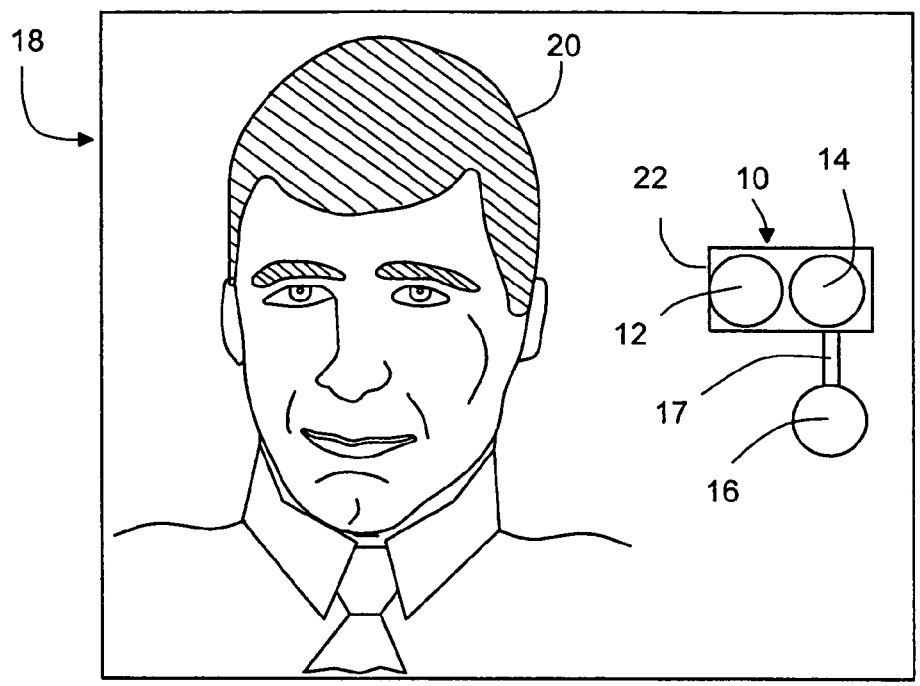
FIG. 1 is a schematic representation of a field of view of a thermal imaging device in which the field of view includes the subject whose thermal image is to be acquired and an in-frame temperature reference system.
Figure 2:
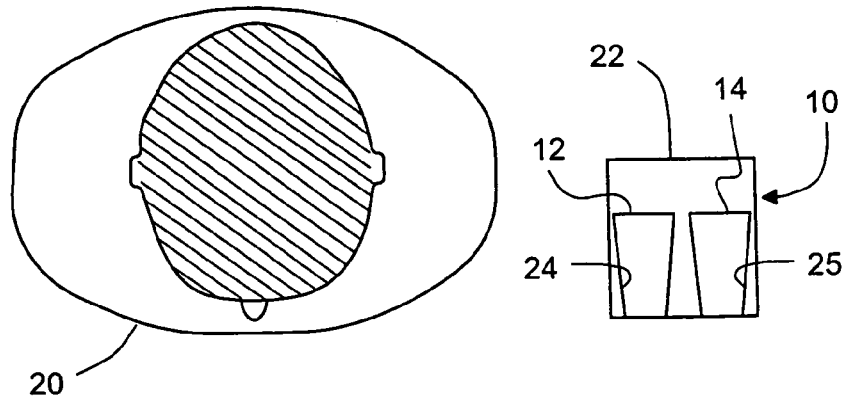
FIG. 2 is a top view of the subject and temperature reference system of FIG. 1.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

As an overview, the present invention involves acquiring thermal image data for one or more subjects and then using the thermal image data to derive temperature information about the subject(s). The acquisition of thermal image data involves using appropriate equipment and optionally the use of suitable reference temperature information to help enhance the accuracy of the acquired data. The derivation of core body temperature information may involve one or more of data calibration (such as with respect to the reference temperature data), image processing, identifying area(s) of the image from which to derive the desired temperature information, and deriving the desired temperature information using an appropriate thermal model. The derived temperature information has many useful applications. These features of the present invention will now be described in more detail.

Thermal imaging data generally may be acquired by using a digital thermal image capture device such as a thermal camera. In the past, thermal cameras were large and expensive. They typically provided an analog display with documentation only via film camera attachments. The thermal detectors required liquid nitrogen to obtain low operating temperatures. Portability was limited due to the large and heavy battery packs. The price of these older thermal, infrared cameras ranged from $50,000 to $60,000.

Recent solid state developments now provide hand-held, digital thermal imaging cameras that resemble an oversized, 35 mm film camera. They operate at room temperature without expensive cooling systems. An example of such a solid-state, uncooled, digital thermal imaging camera is commercially available under the IR SnapShot® trade designation from Infrared Solutions, Inc. This camera is based on Honeywell infrared (IR) thermoelectric thermal array detector technology. It is an imaging radiometer, which means it is an infrared camera that acquires a thermal image of a scene and can determine the temperature of any pixel within that scene. With the push of an electronic button, a 120-element linear thermoelectric detector array scans across the focal plane of a germanium IR lens in approximately 1.6 seconds. Camera software stores a thermal image, 120×120 pixels, within the camera in flash memory cards. The camera can also download the images directly to a laptop or desktop computer for storage or post-processing. The calibrated thermal images may be displayed with numerous colormaps on either the color LCD display of the camera or in computer displays. The price of the IR Snap-Shot, thermal imaging camera currently is about $13,400.

Radiometric IR cameras that operate at a video rate also are becoming available. These cameras provide calibrated thermal images at the faster, video rate of 30 frames per second. Typically, the thermal images may be viewed in real time at the video rate with a freeze frame capability. One may store, download, and process the selected frames.

Thermal images from radiometric cameras, still or video, provide a volume of temperature information for thermal analysis and processing. The data may be represented as a matrix of temperatures in which each element corresponds to a pixel in the thermal image. These pixels, in turn can be used to measure the temperature of anatomical features when the subject of the image is the test animal or patient. Image processing techniques may be applied to the temperature matrices as with any other matrix.

Preferably, thermal image data is acquired using one or more temperature references that allow the data to be accurately calibrated. Such references may be out of frame (e.g., incorporated into the camera), or in frame (e.g., captured within the frame of view of the acquired image. For instance, the accuracy of a calculated core body temperature, $T_0$, is dependent upon both the accuracy of a skin temperature measurement and the accuracy of the ambient temperature measurement near the skin surface. While not essential to the invention, a preferred embodiment of the present invention involves using two or even three in-frame temperature references to increase accuracy of the thermal image data and subsequent derivation of temperature information from that data.

FIGS. 1 through 5 schematically shows a frame 18 of the field of view of a thermal imaging device (not shown) in which frame 18 includes a subject 20 whose thermal image is to be acquired and an in-frame temperature reference system 10. Temperature reference system 10 includes multiple black body temperature references 12 and 14. Optionally, a third reference 16 may be incorporated into the frame 18 for purposes of providing an ambient temperature reference. High accuracy for skin temperatures may be achieved by providing dual-temperature, infrared blackbody references 12 and 14 within the field of view of the thermal imaging camera (not shown). Note that temperature references 12 and 14 are positioned inside housing 22 and are viewable via channels 24 and 25. The temperature references 12 and 14 help to enable a precise calibration of each image at the digital image processing level.

Preferably, one blackbody reference 12 would be at a first temperature below the expected minimum skin temperature of subject 20, and the other reference 14 would be at a second temperature above the expected maximum skin temperature of subject 20. This allows, for instance, a linear calibration between the two reference temperatures. For those embodiments of blackbody references 12 and 14 that employ heaters (most cost-effective), the reference temperatures preferably are above the ambient temperature. If the ambient temperature is elevated significantly above a normal room temperature of 70° F., the two reference temperatures may need to be at or above the skin temperatures.

The heat transfer model discussed below in connection with FIG. 9 also may require an accurate ambient temperature input. Consequently, an ambient temperature reference 16, for example a thin plate, thermocouple or RTD, is positioned near the blackbody references 12 and 14 so that reference 16 appears in the frame along with the blackbody references 12 and 14. As shown, reference 16 is supported outside housing 22 upon a thermally insulating support 17. This approach provides an ambient temperature reference in the image frame and provides the measurement of ambient temperature in close proximity to the target, thus avoiding temperature errors due to differences in ambient temperature between the camera and the target.

While the use of an ambient temperature reference in an image is a preferred approach, other approaches may also be used. For example, an ambient temperature probe may be located at the camera. Although requiring digitization of the temperature signal, this approach does provide the necessary, continuous ambient temperature measurement to feed into the heat transfer model equation. The time response of such a temperature probe is preferably fast enough to accurately track changes in ambient temperature.

Figure 3:
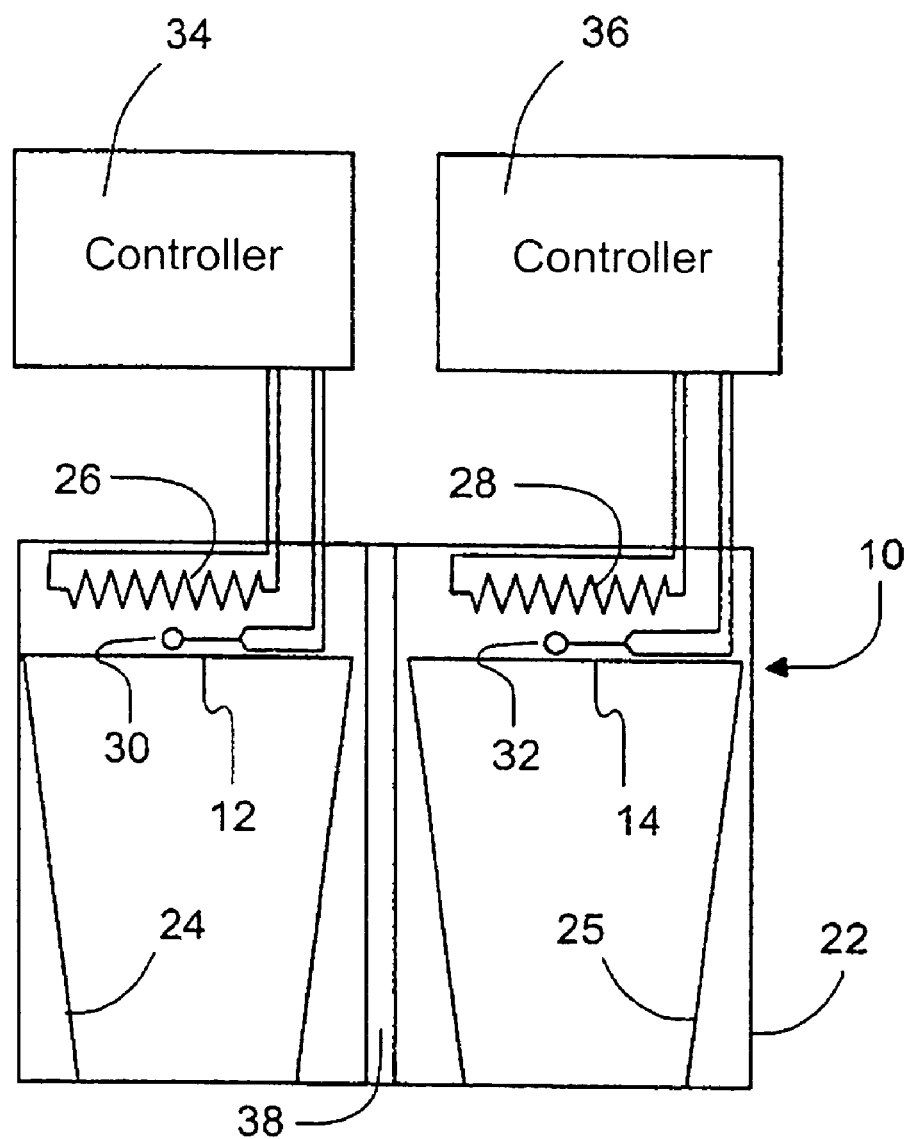
FIG. 3 is a schematic top view showing more details of the temperature reference system of FIG. 1.
Figure 4:
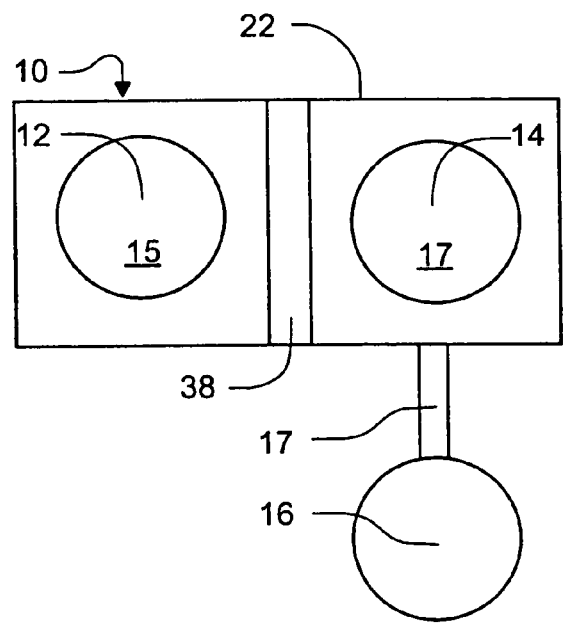
FIG. 4 is a schematic front view showing more details of the temperature reference system of FIG. 1.
Figure 5:
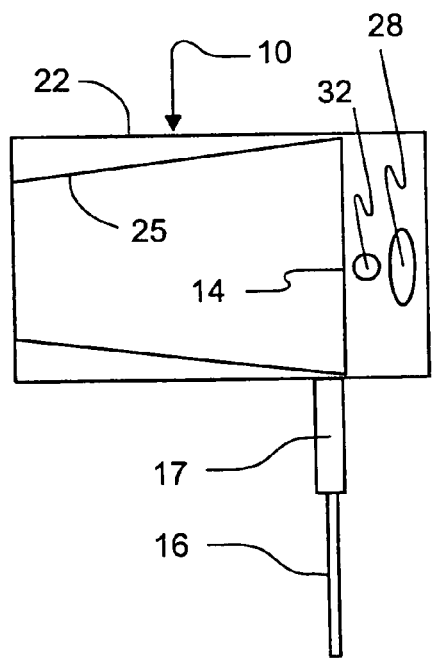
FIG. 5 is a schematic side view showing more details of the temperature reference system of FIG. 1.

FIGS. 3 through 5 show temperature system 10 in more detail. Each infrared, black body reference 12 and 14 has its own heating element 26 and 28, feedback temperature sensor 30 and 32, and controller 34 and 36, respectively. An insulating member 38 helps to thermally isolate one black body reference 12 from the other black body reference 14 to minimize thermal cross talk. The references 12 and 14 each have a respective surface 15 and 17, respectively, with an emissivity as close to unity (1.00) as is possible to avoid reflections. Each of channels 24 and 25 is in the form of a tapered cylinder. Channels 24 and 25 significantly reduce the amount of background infrared energy that enters the source and reflects back in the direction of the thermal camera lens. The controllers 34 and 36 help to maintain the surface temperature of the references 12 and 14 at the desired, pre-selected, reference temperatures. The use of two such temperature references in this manner could be used to calibrate a thermal image with much tighter tolerances than is achievable by an IR camera alone. Housing 22 may be formed from an aluminum block with black, anodized surfaces.

While the reference temperature approach of FIGS. 1 through 5 is likely to improve the absolute accuracy of the skin temperature measurement, it does not address the temperature difference between various skin regions, nor the variation of skin temperature with variations in ambient temperature. Aspects of accommodating temperature differences among skin regions and the impact of ambient temperature are discussed further below.

FIGS. 1 through 5 show a reference temperature approach that uses two independent blackbody references 12 and 14 set at two distinct reference temperatures. A second approach could involve a single temperature source coupled to surfaces having different emissivity values. This alternative method simplifies the electrical control requirements from two units to one unit and avoids the insulation requirements between references maintained at different temperatures.

Figure 6:
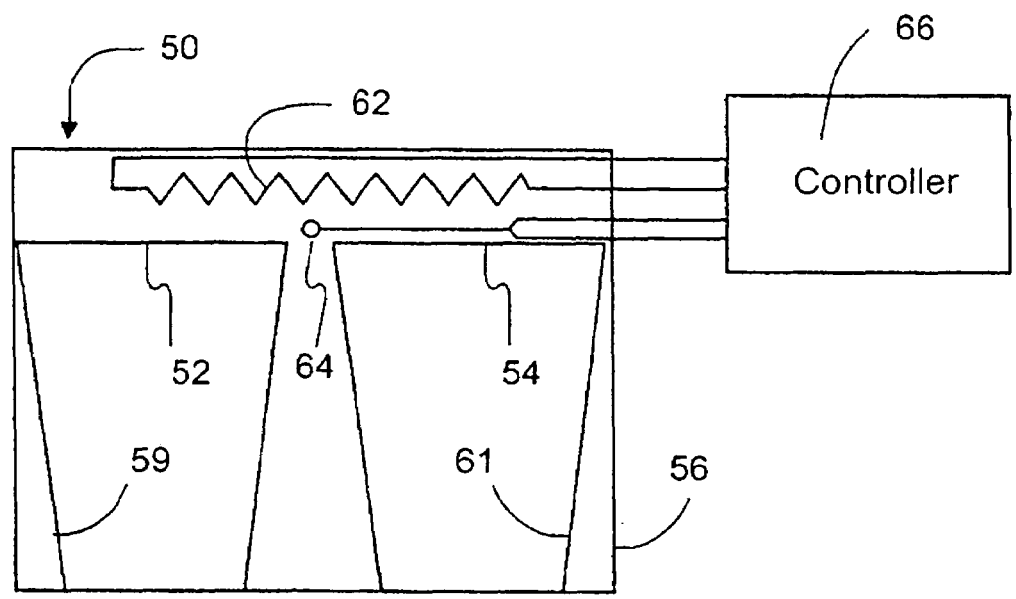
FIG. 6 is a schematic top view of an alternative temperature reference system useful for providing in-frame temperature references in the practice of the present invention.
Figure 7:
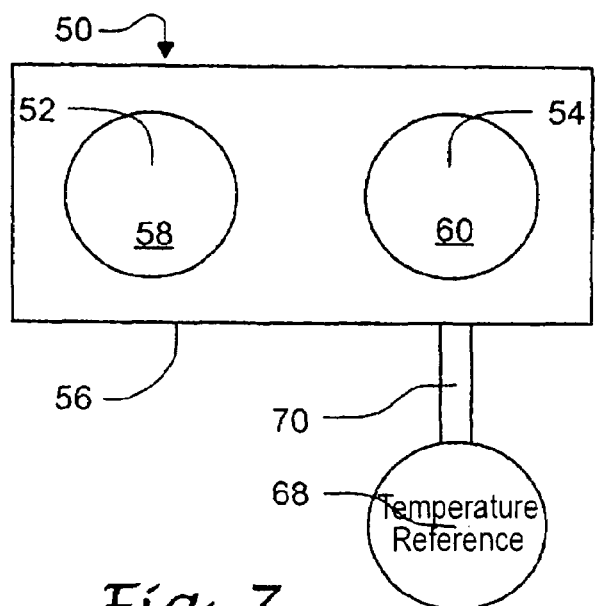
FIG. 7 is a schematic front view of the temperature reference system of FIG. 6.
Figure 8:
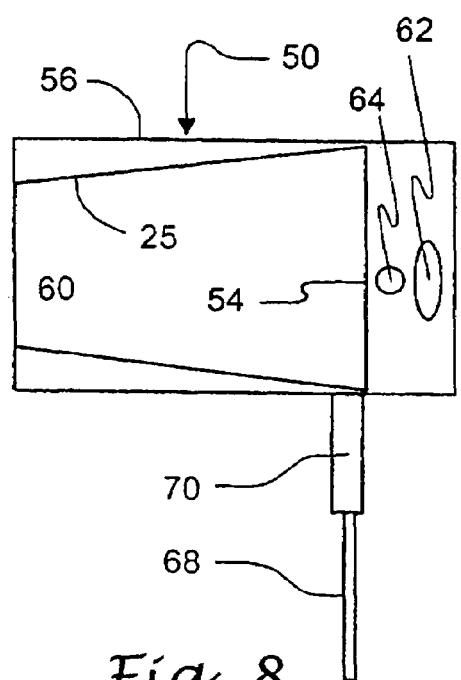
FIG. 8 is a schematic front view of the temperature reference system of FIG. 6.

This alternative approach is shown schematically by temperature system 50 of FIGS. 6 through 8. System 50 includes temperature references 52 and 54 contained in housing 56. Each of references 52 and 54 has a surface 58 and 60, respectively, visible from the thermal imaging camera as indicated best in FIG. 7. One of these surfaces, for instance surface 58, has a higher emissivity, $\epsilon_{hi}$, preferably near unity (1.00). The other surface, for instance surface 60, has a lower emissivity, $\epsilon_{low}$.

When surface 60 has an emissivity less than unity, the radiation efficiency of the reference surface 60 is less than 100%. Thus, the infrared camera (not shown) detects a lower level of infrared energy. The camera interprets the lower level of IR energy as a lower temperature. If the emissivity of two reference surfaces is tightly controlled, two apparently different reference temperatures may be achieved from a block maintained at a uniform temperature. In the apparently lower temperature reference, most reflected IR energy is advantageously captured and not reflected to the camera. This may be accomplished via the tapered channel through which the reference is viewable. A primary advantage of this approach for this application is that the block may be controlled at a temperature greater than ambient temperature and above the upper expected skin temperature while the lower reference temperature may actually be less than ambient temperature. This is a feature not as easily achieved with the independent blackbody sources.

Tapered channels 59 and 61 provide viewable access to references 52 and 54. Housing 56 may be formed from an aluminum block with black, anodized surfaces. A single heating element 62, feedback temperature sensor 64, and controller 66 are used. No insulation is required between the two references because they are controlled at the same temperature. The apparent difference in temperature is achieved by using surfaces with different emissivities.

An ambient temperature reference 68 is placed near housing 56. For purposes of illustration, reference 68 is mounted to housing 56 via a thermally insulating support 70. In this particular embodiment, the ambient reference may be a thin, anodized, aluminum disc having an anodized black surface. Such a disc will tend to rapidly attain ambient temperature. The black surface (with respect to infrared) is useful to minimize reflected energy. The position of the ambient reference 68 below the housing 56 for the dual temperature references 52 and 54 is intentional. By placing the ambient reference 68 below the heated housing 56 on an insulated support 70, the ambient reference 68 is insulated from unintentional heating by either convection or conduction from the elevated temperatures within housing 56. As shown, the ambient reference 68 is not housed and viewable through a channel such as a tapered channel as is shown for the other references. As an option, ambient reference 68 could be housed and viewable through such a tapered channel if desired, e.g., for additional rejection of reflected energy.

The advantages of system 50 are numerous. Only one heater element 62, feedback temperature sensor 64, and controller 66 are required. No insulation is required between the two references 52 and 54 since they are controlled at the same temperature. The low temperature reference (either reference 52 or 54 as the case may be) may be below the ambient temperature while the high temperature reference may be above the expected upper skin temperature. While this description thus far has discussed a reference system with two housed reference surfaces, it will be appreciated that different numbers of temperature references may be used, with each reference being associated with a different surface emissivity value.

While the above description of the present invention includes in-frame temperature references, it should be noted that these references are only desirable as when the thermal imaging hardware does not possess sufficient accuracy on its own. When a thermal imaging device has a level of accuracy with absolute surface temperature errors in the range of 0.1° to 0.5° F. (or better), then the in-frame temperature references may be omitted.

Temperature probes may also be used in place of the ambient reference as shown. However, such temperature probes complicate the data acquisition, timing alignment and calibration procedure. Accuracy and simplicity result from having three calibration levels on each and every image.

The in-frame temperature references of the present invention, such as the independent references shown in FIGS. 3-5 or the different emissivity surfaces of FIGS. 6-8, may be maintained at a fixed temperature that is maintained accurately without additional control from the camera system. Such fixed references would be periodically calibrated and used as a standard.

As an alternative to using a fixed reference temperature standard is a variable reference with feedback to the camera system. Such a variable reference might be under programmable control. It will be appreciated that numerous combinations of temperature settings, programmability, and even telemetry may be used.

Temperature information may be directly derived from the thermal image data. More preferably, though, the thermal image data first is manipulated in one or more ways to facilitate temperature derivation. Exemplary manipulations include data calibration, correcting measured temperature for emissivity of a surface, image processing (such as resolution enhancement), and identifying target areas of the image from which to derive temperature information. For instance, the following discussion explains why targeting the eye or forehead regions is useful when it is desired to derive core body temperature from thermal image data.

The preferred measurement sites for deriving core body temperature from thermal image data in accordance with the present invention desirably have no or minimal vasoactive response, high thermal coupling to core body temperatures, and a prominent location. While the ideal surface does not exist in practice, better targets provide acceptable tradeoffs and compromises.

Choosing target areas with minimal vasoactive effects is highly desirable. Within a living body, heat transfer is tightly linked to blood circulation or tissue perfusion. Heat transfer due to circulation is 100 times more significant than that due to conduction. This is both an advantage and disadvantage to the present invention. Positively, this means that regions of the body that are remotely located from the core may be at core temperature or at least tightly coupled to core temperature as long as the distal region has a significant blood supply. Negatively, variations in circulation due to vascular constriction or dilation may also vary the thermal properties of a given region. Based upon these criteria, the preferred measurement sites should have adequate perfusion with minimal neurological control of arterial constriction or dilation.

A better target area also has high thermal coupling to core body temperature. As previously discussed, one key component associated with heat transfer within the living body is blood circulation. Two anatomical sites that are separated by distance, but are both highly perfused, are likely to exhibit similar temperatures and similar changes in temperature. Other thermal uniformities are likely to exist due to thermal conduction through specific liquid volumes within the body such as blood within cardiac chambers, urine within the bladder, cerebral-spinal fluid within the spinal cord and brain, and the vitreous humor within the eye. These fluid volumes are likely to maintain uniform temperatures due to thermal conduction within the fluid volume and close proximity to the circulatory system.

A practical requirement for a useful measurement site is that the surface region be prominent and easily accessible for monitoring. While bladder temperatures may be uniform around the surface of the bladder, such an internal organ does not lend itself to thermal imaging under routine screening conditions. Body regions commonly covered by clothing are also less desirable for screening applications. Though the tympanic membrane of the ear has been found to be a useful measurement site for infrared monitoring of temperature, the close personal contact involved with acquiring data from within the ear canal is a disadvantage for mass patient screening, especially, if the disease is highly contagious and deadly.

Another practical consideration for the selection of a measurement site is the thermal control of the surface. Common activities such as hand washing, handshakes, or transporting hot and cold beverages subject some sites, such as the hands, to thermal variations that are unrelated to the core body temperature of the patient. Heavy makeup may alter the thermal properties of the cheeks and lips.

Consequently, two regions of the body are preferred candidates for targeting for purposes of the acquisition of surface temperature as applied within this invention, namely, the forehead and the region of the eyes. The forehead region has the most advantages for mass scanning applications while eye temperatures provide additional options.

The forehead excels as a skin region to target for the purposes of this invention. The forehead is in close proximity to the brain, the organ exhibiting the highest and most critical, thermal control within the body. The forehead and scalp region of the head have minimal vasoconstrictive function for cold ambient conditions. This is why the head loses substantial amounts of heat in cold conditions. The prominence of the forehead also makes it attractive from a practical viewpoint. A view of the forehead is seldom obstructed by clothing that cannot be conveniently removed. The forehead also exhibits lesser levels of makeup or jewelry than other facial regions.

The eye region may also preferably be used to target thermal surface temperatures. The eyelids and blink response maintain a fairly uniform moisture content on the corneal surface, thus controlling the thermal properties of the surface. The fluid volume (vitreous humor) within the eye stabilizes the thermal properties of the cornea and also provides thermal conductivity to the internal regions of the head and brain. Practical concerns such as heavy eye makeup and contact lenses may affect measurement accuracy. Additionally, eyeglasses must be removed prior to an eye measurement. However, cultural dress that might obscure the forehead, such as Muslim vales, need not restrict eye scans.

Image calibration and processing may be desirable before deriving temperature information from a thermal image. Numerous image processing techniques are helpful in the implementation of this invention and are known to those skilled in the art. The telltale shape of a head, either individually or in a group may be used to automatically locate the forehead and eye regions. Frequently the eyes are associated with the highest temperature present within the image of a face.

In order to obtain accurate thermal measurements with infrared cameras it is desirable to be alert to resolution effects. Unlike standard, visible spectrum cameras with 1 to 5 million pixels in an image, infrared technology presently provides images with perhaps 120×120 (14,400) pixels. While admirable in thermal perspective, it is not yet on par with photographic resolution. For large objects the resolution of thermal images is of little consequence. However, for small objects or narrow features, such as eyes in this project, it is necessary to consider resolution effects. Resolution enhancement algorithms are useful to improve the selectivity and averaging capability of the algorithms. Image filtering may be used to reduce thermal noise, accentuate edges, or identify facial landmarks. Various calculations of temperature such as peak, mean or median may be used when empirically determined to improve reliability.

Image resolution may be enhanced, for instance, by applying image interpolation techniques such as one or two dimensional spline fits to the image data. Using custom processing routines, the resolution of the thermal images may be enhanced from 120×120 pixels to 953×953 pixels. This increases the number of temperature points in an image from 14,400 points to 908,209 points.

Infrared emissivity is a measure of the infrared radiating efficiency of a surface. A perfect radiator has an emissivity value of unity, 1.00. Highly reflective surfaces, such as polished metals, may have emissivity values of 0.10 or lower. Human skin has an emissivity of approximately 0.96. Using actual emissivity characteristics of a surface, a measured surface temperature may be converted to a corrected surface temperature measurement via a formula such as that shown below:

$$T_{K2} = \left( \left( \frac{1}{\varepsilon_2} \right) (-(1-\varepsilon_2) T_{bK}^4 + T_{K1}^4) \right)^{0.25} \quad (1)$$

where $T_{K1}$ is the measured surface temperature in degrees Kelvin; $T_{bK}$ is the background or ambient temperature in degrees Kelvin; $\varepsilon_2$ is the actual surface emissivity; and $T_{K2}$ is the surface temperature corrected for emissivity. It is important to note that all calculations are conducted in absolute temperature units of Kelvin. The corrected surface temperature measurement may then be used to derive other temperature information of the subject, such as core body temperature.

The use of temperature references, preferably the multiple, in-frame temperature references discussed above, allows the skin or surface temperature measurements to be accurately calibrated for each image. An illustrative calibration equation is indicated in the following Equation:

$$T_{Scorr} = m_1 T_S + C_1 \quad (2)$$

where $T_{Scorr}$ is the calibrated surface temperature; $m_1$ is the slope of the calibration equation derived from the actual temperatures of the reference surfaces and the temperatures of those surfaces as measured by the thermal imaging camera; $T_S$ is the surface temperature of the target area from the thermal camera prior to calibration and optionally after surface emissivity correction; and $C_1$ is the offset or y-intercept for the calibration equation derived from the actual temperatures of the reference surfaces and the temperatures of those surfaces as measured by the thermal imaging camera.

As an example, let the uncalibrated IR camera surface temperatures, $T_s$, be 85.6° and 92.4° F. for the calibrated temperatures, $T_{Scorr}$, 88.0° and 95.0° F., respectively. For these errors the calibration equation becomes:

$$T_{Scorr} = 1.02 T_S + 0.72 \quad (3)$$

As discussed herein, the accuracy of a calculated core body temperature measurement, $T_0$, is dependent, in part, upon the accuracy of the ambient temperature measurement. As shown below in equation (4) the core body temperature, $T_0$, is a function of both surface temperature, $T_s$, and ambient temperature, $T_a$. For this reason the present invention preferably uses an ambient temperature reference in each image. The accuracy of the ambient temperature, as measured via the IR camera for instance, may be improved by correcting for surface emissivity and calibration correction per the in-frame reference(s). In the event that even greater ambient temperature accuracy is desired or necessary, multiple temperature references using multiple emissivity surfaces may be extended to provide lower temperature references. These additional references may be closer to the anticipated ambient temperature.

Temperature information is readily derived from the thermal image data, as corrected, calibrated, enhanced, or otherwise modified as desired. A simple heat transfer model 100 is now described with reference to FIG. 9. This model 100 permits the computation of core body temperature, $T_{core}$, knowing the surface skin temperature, $T_{skin}$, and ambient temperatures, $T_{ambient}$, provided by thermal imaging. Thermal resistance, $R_1$, represents the thermal resistance attributable to the arteries, arterioles, and skin between the core temperature of the body and the skin surface visible to the thermal camera. The thermal resistance between the skin surface and the ambient air is represented by $R_2$. Skin temperatures are known to change with changes in ambient or air temperatures. By accounting for ambient temperature, this model permits the conversion of confusing skin temperatures to clinically useful core body temperatures.

Figure 9:
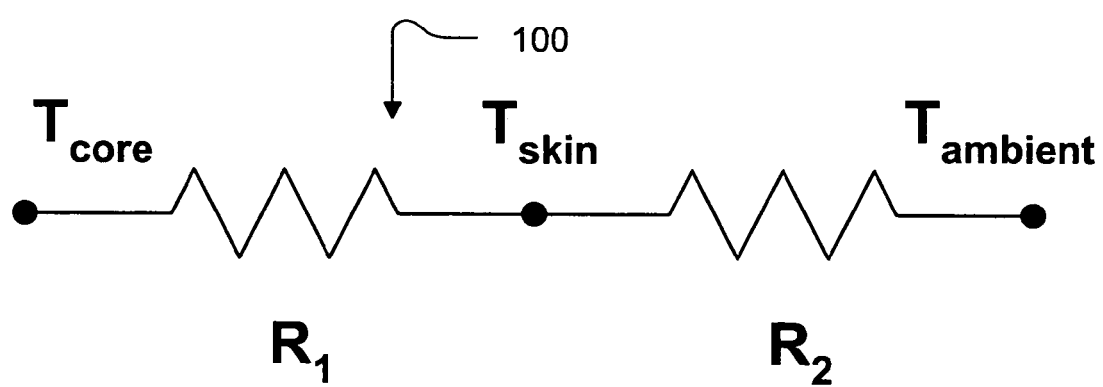
FIG. 9 schematically shows a heat transfer model showing a relationship between ambient, skin, and core body temperatures.

Optionally, the model 100 shown in FIG. 9 may be enhanced with the addition of capacitance at the core and skin nodes to take thermal masses into account. Since heat transfer in the human body is tightly linked to circulation, arterial and venous blood flow to a selected skin region might also be included in a more complex, thermodynamic model. This model may also be modified to account for changes in humidity, which may change the thermal resistance between the skin surface and the ambient air.

Using the model of FIG. 9, a formula to calculate core body temperature from ambient and skin temperature is given by the following equation:

$$T_o = \left( \frac{T_S - T_A}{K_1} \right) + T_A; \quad (4)$$

where $T_0$ is the core body temperature; $T_s$ is the surface skin temperature in the selected region (which may have been calibrated and/or corrected for emissivity); $T_A$ is the ambient temperature; and $K_1$ is the resistive ratio as shown below:

$$K_1 = \left( \frac{R_2}{R_1 + R_2} \right); \quad (5)$$

where $R_1$ and $R_2$ are as previously defined.

$K_1$ may be empirically determined as follows:

$$K_1 = \left( \frac{T_S - T_A}{T_0 - T_A} \right); \quad (6)$$

where the variables are as defined for equation (4). The accuracy of $K_1$ may be enhanced by averaging the application of equation (6) over a range of core and surface temperatures. A value for $K_1$ may thus be determined empirically from measurements of $T_0$, $T_s$, and $T_A$.

Since the core body temperature, $T_0$, may be obtained via oral, axillary, rectal or tympanic measurements, it should be noted that the calibration constant, $K_1$, may vary according to the method of core body temperature measurement in that there are variations in the physiological 'core body temperature' to which the above measurements are ultimately compared. Core body temperature is commonly measured by minimally invasive means such as oral, rectal, axillary or tympanic methods. Invasive techniques may yield arterial temperatures and venous temperatures at various sites throughout the circulatory system. While 'core body temperature' is often thought of as a singular value, the body is actually functioning at a constantly changing set of temperatures within the limits established by its thermoregulatory system. For example, rectal temperatures typically register 0.5 to 1.0° F. above oral temperatures and may lag changes in oral temperature by 1-2 hours. Arterial temperatures filled with blood from the heart are typically higher than venous temperatures containing blood returning from cooler peripheral sites of the body.

While equation (6) shows $K_1$ to be only a function of $T_0$, $T_s$, and $T_A$, it is envisioned by this invention that the empirical determination of $K_1$ may include the introduction of other variables such as humidity. It is anticipated that equation (6) will be valid for low or mid-range humidity, but it is recognized that as humidity increases, the value of $K_1$ is likely to change since the thermal resistance, $R_2$, is at least partially dependent on the humidity. $K_1$ may also be empirically modified to account for changes in blood circulation, one of the factors that control the transfer of heat form the core to the skin.

A general calibration equation is as follows:

$$T_0 = \left(\frac{T_S - T_A}{K_1}\right) + T_A + T_{offset} \qquad (7)$$

where $T_0$ is the core body temperature; $T_s$ is the surface skin temperature obtained via thermal imaging techniques; $T_A$ is the ambient temperature; $K_1$ is the empirically determined calibration constant; and $T_{offset}$ is an offset term that accounts for any offset error inherent in the thermal imaging system. Ideally, the value of $T_{offset}$ would be zero.

Figure 10:
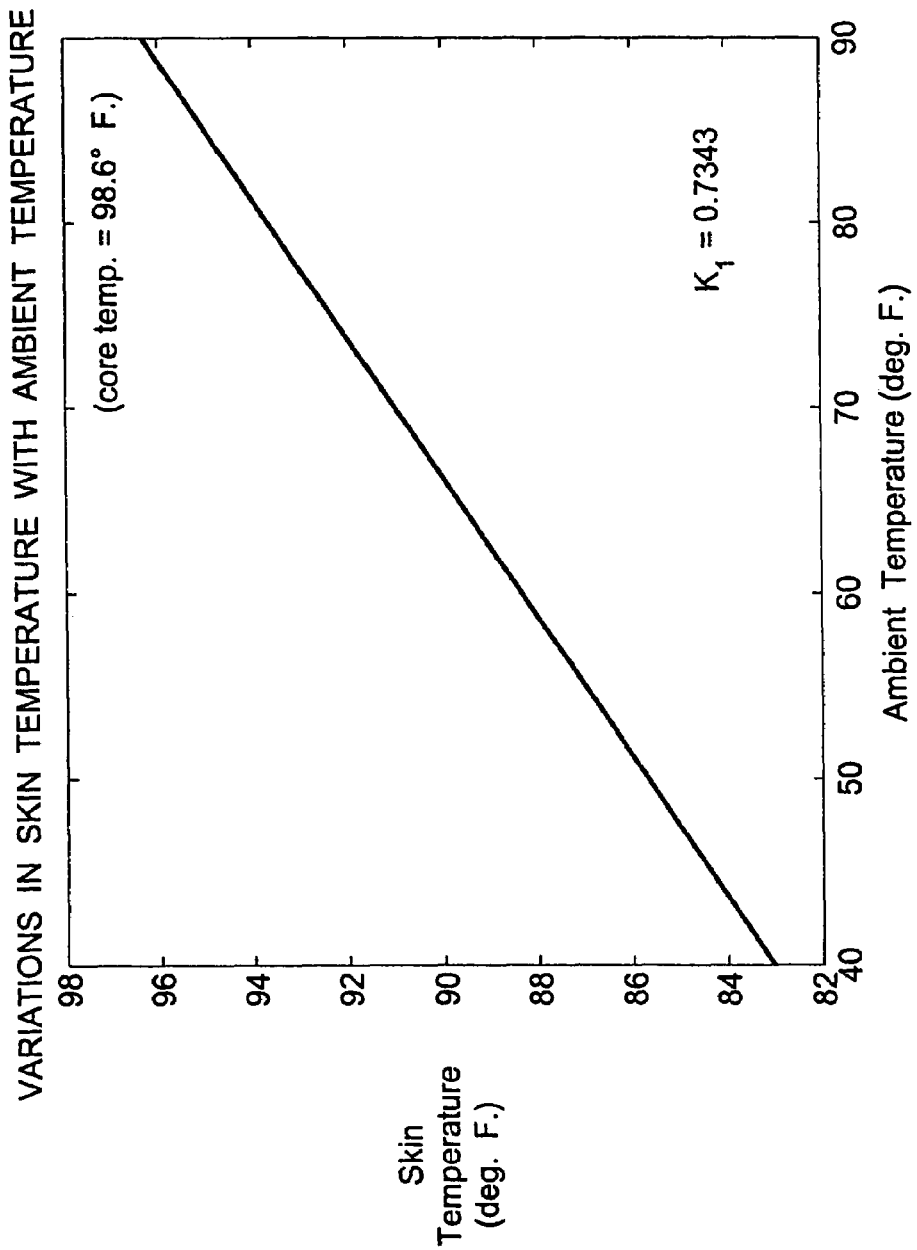
FIG. 10 is a graph showing a theoretical variation of skin temperature with ambient temperature.

The importance of accounting for the impact of ambient temperature upon a derivation of core body temperature is shown in the following equation and in FIGS. 10 and 11. The following equation is derived by solving Equation (4) for $T_s$ with the variables as previously defined.

$$T_s = K_1(T_0 - T_A) + T_A; \qquad (8)$$

It is apparent from this equation and intuitively apparent that the skin temperature of a healthy person will vary with ambient temperature. While the core body temperature may remain constant at 98.6° F., the skin temperature will be significantly different with different ambient temperatures. FIG. 10 shows the variation of skin temperature with ambient temperature in accordance with Equation (8), over a range of ambient temperatures from 40° F. to 90° F.

Figure 11:
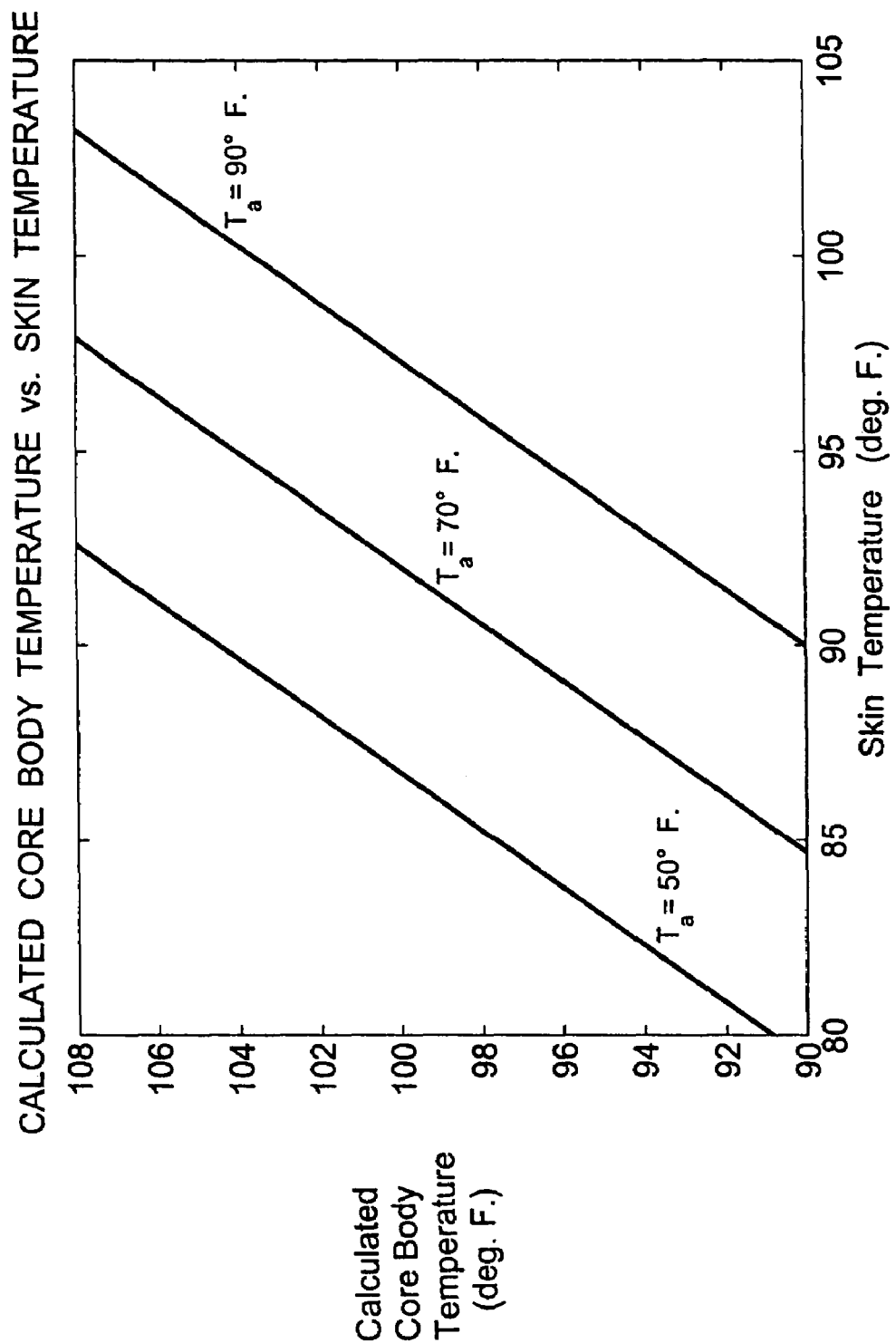
FIG. 11 is a graph showing a theoretical variation of calculated core body temperature with respect to skin temperature for various ambient temperatures.

FIG. 11 shows the effect that ambient temperature has on the calibration of the relationship between skin temperature and core body temperature. A skin temperature of 91° F. corresponds to a core body temperature of 98.6° F. when the ambient temperature is 70° F. (center curve). However, when the ambient temperature drops to 50° F. a skin temperature of 91° F. corresponds to a core body temperature of 105.8° F. (left curve). When the ambient temperature increases to 90° F. a skin temperature of 91° F. corresponds to a core body temperature of 91.4° F. (right curve).

When the ambient temperature is significantly below the core body temperature the simple thermal model appears valid. However, as the ambient temperature approaches the core body temperature with values at or above 90° F., the model may require modification to account for perspiration effects. It is likely that empirical data will dictate that calibration 'constant', $K_1$, becomes a function of ambient temperature and humidity in order to account for evaporation effects.

Image processing software may be written in different programming languages, for example C++ or an equivalent programming language. The image processing software may reside in the imaging camera. Such resident programs would make analysis and output very fast and convenient. The image processing software may also reside in a processor separate from the camera, for example a separate computer such as a desktop or laptop computer. Data manipulations or modifications and derivation of information is readily accomplished by downloading the images to a desktop or laptop computer running software suitable for manipulating and analyzing the data. For example, analysis software available under the trade designation MATLAB can be used to write the custom algorithms described herein. The hardware, software and user interfaces are convenient and available via the MATLAB software.

The technology used to implement remote, core body temperature monitoring via thermal imaging techniques has numerous applications. The following applications are illustrative of the present invention and are not meant to be exhaustive or limiting in scope.

One of the most urgent applications of this invention is the screening for subjects with severe acute respiratory syndrome (SARS). This new disease is highly contagious, with an estimated death rate of 20% for the population in general and as high as 40% for those over 60 years of age. Since an early symptom of SARS is a fever of 100.4° F. or higher, the present invention may be used to screen persons for an elevated body temperature. Those found to exhibit a fever may be checked by medical personnel for more detailed diagnostics. This type of screening may be conducted at nearly any location where the identification of SARS subjects is deemed useful.

Since the present invention provides a core body temperature measurement from thermal imaging data, it may be used for screening numerous human diseases whose symptoms include an elevated body temperature or fever. With the current threat of biological terrorism and naturally occurring diseases, the uses for this invention are widespread. One example involves airport security. Since dangerous microbes may be spread intentionally or unintentionally by travelers, airports are a good application of the present invention. Current airport screening technologies detect guns, knives, and explosives, but are of little value against biological threats. The present invention helps to fill this gap.

Standard medical diagnostic techniques are time-consuming and unsuited for mass screening at places such as airports, ports of entry, immigration stations, crowded malls, or places of business. Under threats of contagious diseases and biological weapons nations, states, cities and communities seek to secure their borders from such danger. The present invention is well-suited to help identify those persons which may introduce biological threats across national, state, city or community borders or other ports of entry.

Business may also find the present invention to be useful. In addition to security concerns similar to nations, states and cities described previously, numerous business have sanitation and cleanliness concerns regarding employees and products. Restaurants might take advantage of the present invention to screen employees to avoid food contamination;

pacemaker companies may screen employees working in clean rooms to avoid potential contamination of medical products; and sales staff returning from specific regions of the world may be screened.

The present invention may also be useful to help protect governmental buildings. Since government buildings are prime targets for terrorism, the present invention may be used to help identify bio-terrorism threats perpetrated against such facilities. Additionally, it may be used to screen employees for more routine contagious illnesses. The present invention may also fits into the security strategy for embassies in foreign countries. Immigration offices are another place where contagious diseases or biological weapons may appear.

The present invention would also be useful for hospitals, clinics, and emergency medicine. Hospitals have numerous screening applications. The present invention may be a useful triage tool in emergency rooms and clinics where it is advantageous to quickly isolate contagious patients before they spread disease to hospital staff or other patients. Ambulance employees may find value in the ability to instantly evaluate accident victims for fever symptoms.

Public places where large groups of people congregate, such as malls, convention halls and churches may find the present invention useful in the event that diseases or biological weapons escalate to epidemic proportions.

Any public facility may make use of the present invention to identify victims of diseases or biological weapons for isolation and treatment.

Numerous diseases or conditions have an elevated core body temperature as a symptom. The present invention is useful for noninvasive screening or monitoring. This might take the form of temperature monitoring during the night without waking the patient, or screening emergency room patients for contagious diseases indicated by the presence of fever. This invention might be applied anywhere present clinical methods of measuring body temperature are employed. The greatest advantage will reside with those applications where remote or rapid measurements are desired.

While most of the applications discussed herein deal with hyperthermic conditions, the present invention is also useful to detect and measure hypothermia. This hypothermia may result from surgery or exposure to a cold environment prior to arriving at a medical facility.

While the present invention was designed with live subjects in mind, it may also prove useful to forensic investigators to help determine the time of death. After death, the temperature of the human body is a function of its initial temperature, the ambient temperature, humidity and the time since death occurred. The present invention may be useful in a product specifically designed to calculate time of death based upon the parameters discussed within this application.

While the present invention has been described above primarily for human applications, this invention applies equally well to animal applications. Any animal disease or condition which has as a primary symptom, the elevation of core body temperature, may be detected with this invention. The invention may be used to detect an elevated core body temperature or fever in wildlife, livestock, zoo animals, raptors, game birds, and many other type of animals.

If captured wildlife or domestic livestock are individually confined in a small chute, a thermal imaging system composed of an infrared camera, personal computer (PC), and custom analysis software may be used to diagnose the live animal under test. The in-frame thermal references may be placed in a convenient location near the edge of the image. This equipment may be set up in a small room adjacent to the animal pens or temporarily set up on tripods in a field. Thermal images of sufficient resolution may be obtained from a distance of 8 to 12 feet. While still cameras are sufficient, thermal video monitoring with still-image capture provides even greater convenience in acquiring accurate images. The thermal images may be downloaded to a computer, such as a desktop or laptop PC for storage and analysis. A nearly instantaneous diagnosis may be obtained if the custom analysis software is resident in the PC. This analysis software implements the algorithms of this invention. An instantaneous, positive live diagnosis enables handlers to immediately isolate the animal. This avoids the inconvenience of having to recapture the animal at a later time. It also eliminates hours or weeks of herd contact with an infected animal, as would be common waiting for results from laboratory tests.

Commercial herds of deer, elk or domestic livestock may be manually scanned with a thermal imaging system as described herein. This entails capturing or confining herd animals individually and then obtaining thermal images as previously described.

However, once thermal camera technology obtains sufficient accuracy to function without the in-frame thermal references, greater convenience for commercial ranchers is possible by adding a longer infrared lens capable of imaging the animals while they are roaming in the pens. This greater magnification, available for either still or video cameras, provides image acquisition at distances of 20 to 150 feet depending upon the specifications of the IR lens. Analysis follows, as described previously, after downloading the images to a PC containing the custom analysis software.

With this approach, live animal diagnosis has been transformed from a high-risk, capture event (necessary for blood tests) to a remote photography session.

The image acquisition when scanning commercial herds of deer, elk or domestic livestock may be automated. In other words, position sensors and imaging equipment may be set up such that the animals take their own pictures by triggering the position sensors. The equipment and sensors may be strategically placed along chutes near feed troughs or water supplies. The thermal references may be placed in an appropriate location to appear in the thermal image. By conveniently locating a set of position sensors along a well-traveled path, a thermal image may be acquired at the opportune moment when the animal is properly positioned. Image analysis and diagnostics may be performed as previously described. Individual animals may be identified by placing unique thermal patterns on ear tags which will be visible in the images. Such ear tags may use multiple, IR emissivities to create unique, identifiable patterns. Other approaches of identifying the animal may also be used. For example, an RF transponsive identity tag may be located on the animal, perhaps on its ear, and an RF interrogator located nearby the animal to interrogate the identity tag.

The present invention may be used to remotely scan wild animals such as deer and elk. The thermal camera and PC may be made fully portable, permitting live-animal chronic wasting disease (CWD) diagnosis from tree stands, moving vehicles, or on foot. This application is advantageously carried out using an ambient reference and accurate skin temperature readings.

This invention is well suited for culling wild populations of animals such as deer and elk. When included as a modified rifle scope, this invention permits wildlife managers to site a live animal, determine if it is diseased, and immediately take the appropriate action. This application enables culling of only the diseased animals, while leaving the healthy animals alone. Since diseased animals in the wild may only account for a small percentage of the population, this invention eliminates the need to capture or kill a large number of healthy animals in order to remove the diseased animals. This approach is also cost effective by reducing the manpower necessary to move and dispose of the 'healthy' carcasses. This application is advantageously carried out using an ambient reference and accurate skin temperature readings.

As has been discussed, the present invention permits remote, live scanning for elevated body temperatures or fever. The transformation from a laboratory test to a photography session provides even greater opportunities. With the appropriate thermal imaging camera, having sufficient thermal accuracy, this remote monitoring can even be extended to live animal diagnosis from an aircraft. This makes it possible to survey wild or domestic populations from the air. Though the infrared optics for aircraft distances are expensive, the use of the present invention for this unique monitoring application is unavailable from any other technology or laboratory test. This application is advantageously carried out using an ambient reference and accurate skin temperature readings.

This invention is also suited for the remote inspection of zoo animals. Whether used separately or as part of a modified scope on a tranquillizer rifle, this invention permits zoo managers to site a live animal, determine if it is diseased, and immediately take the appropriate action. This application enables darting of only the diseased animals. Since tranquillizers may sometimes be hazardous to valuable zoo animals, this invention minimizes the need to dart, and thus endanger, a healthy animal in order to inspect it for disease. This application is advantageously carried out using an ambient reference and accurate skin temperature readings.

While a measurement of elevated core body temperature is often useful as an initial diagnostic tool, this invention may also be used to track the progress of the fever or disease. Due to the convenience of this live test, it may be used daily or weekly to evaluate the success of a treatment regimen or the progression of a disease.

Since an elevated core body temperature often accompanies avian diseases, applying this invention to birds or raptors should be a useful screening tool, thus avoiding unnecessary stress to the subject and manager.

The use of thermal imaging for the determination of diseases in living beings is described further in U.S. Provisional Patent Application Ser. No. 60/438,644, filed on Jan. 8, 2003 and incorporated herein by reference in its entirety.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A thermal imaging system that provides core body temperature information of a distant subject, comprising
    a first, in-frame temperature reference having a known temperature;
    a thermal imaging device that remotely and noninvasively acquires thermal image data for a field of view that includes at least a portion of a surface of the distant subject and the first, in-frame temperature reference; and
    a processor configured to use thermal image data for the first, in-frame reference and the surface portion to derive a calibrated surface temperature of said surface portion; and
    said processor further configured to derive a core body temperature for the subject using the calibrated surface temperature and the ambient temperature in a manner that accounts for a heat transfer impact of the ambient temperature upon the calibrated surface temperature.

2. The thermal imaging system of claim 1, wherein said processor is further configured to identify a portion of the thermal image data that corresponds to said surface of the subject.

3. The thermal imaging system of claim 2, wherein the surface is an eye region of the subject.

4. The thermal imaging system of claim 2, wherein the surface is a forehead region of the subject.

5. The thermal imaging system of claim 1, wherein the thermal imaging system further comprises an additional in-frame temperature reference that has a known temperature and that is positioned in the field of view of the device when the thermal image of the subject is acquired; and wherein said processor is further configured to use the thermal image data of the additional in-frame reference in order to derive said calibrated surface and a calibrated ambient temperature.

6. The thermal imaging system of claim 5, wherein said processor is further configured to linearly calibrate the thermal image data using temperature data associated with the additional in-frame temperature reference.

7. The thermal imaging system of claim 5, wherein the first and the additional in-frame temperature references are maintained at two distinct temperatures.

8. The thermal imaging system of claim 5, wherein the first and the additional in-frame temperature references have different emissivity characteristics.

9. The thermal imaging system of claim 8, wherein the first and the additional in-frame references are maintained at the same temperature.

10. The thermal imaging system of claim 1, wherein said processor is further configured to derive the calibrated surface temperature using information comprising a measured temperature of the first in-frame reference and the known temperature of the reference.

11. The thermal imaging system of claim 1, wherein said processor is further configured to use an emissivity characteristic to derive the calibrated surface temperature.

12. The thermal imaging system of claim 1, further comprising an ambient temperature reference near the surface portion of the subject, and wherein the frame of view further comprises the ambient temperature reference.

13. A method of remotely and noninvasively determining a core body temperature of a distant subject, comprising:
    remotely and noninvasively acquiring thermal image data for a field of view that comprises at least a portion of a surface of the subject and a first, in-frame reference having a known temperature;
    acquiring an ambient temperature near said surface;
    using the thermal image data for the first, in-frame reference and the surface portion to derive a calibrated surface temperature of the surface portion; and
    deriving the core body temperature of the subject using the calibrated surface portion and ambient temperatures in a manner that accounts for a heat transfer impact of ambient temperature upon the calibrated surface temperature.

14. The method of claim 13, wherein said deriving step comprises using a portion of the thermal image data that corresponds to a target area of the subject to derive the core body temperature.

15. The method of claim 14, wherein the target area is a surface of an eye region of the subject.

16. The method of claim 14, wherein the target area is a forehead region of the subject.

17. The method of claim 13, further comprising an additional in-frame temperature reference in the field of view of the device when the thermal image data of the subject is acquired.

18. The method of claim 17, wherein the calibrating step comprises using a linear calibration algorithm to calibrate the thermal image data of the surface.

19. The method of claim 13, further comprising calibrating the thermal image data for the surface portion using the thermal image data and known temperature data associated with the in-frame temperature references.

20. The method of claim 13, further comprising using an emissivity characteristic of a surface to derive a calibrated temperature for said surface.

21. The method of claim 20, wherein the first in-frame temperature reference is at a temperature higher than an expected value of the surface temperature of the subject and an additional in-frame temperature reference is at a temperature lower than an expected value of the surface temperature of the subject.

22. The method of claim 13, wherein the calibrating step comprises using a linear calibration algorithm to calibrate the thermal image data of the surface.

23. The thermal imaging system of claim 13, further comprising an ambient temperature reference near the surface portion of the subject, and wherein the frame of view further comprises the ambient temperature reference.

24. A method of screening for a fever, comprising:
remotely and noninvasively acquiring thermal image data for a field of view that comprises at least a portion of a surface of a distant subject and a first, in-frame reference having a known temperature;
acquiring an ambient temperature near said surface
using the thermal image data for the first, in-frame reference and the surface portion to derive a calibrated surface temperature of the surface portion; and
deriving the core body temperature of the subject using the calibrated thermal image data surface portion and ambient temperatures in a manner that accounts for a heat transfer impact of the ambient temperature upon the calibrated surface temperature; and
using the determined core body temperature to assess whether the subject may have a fever.

25. A method of screening for a health condition, comprising
remotely and noninvasively acquiring thermal image for a field of view that comprises at least a portion of a surface of a distant subject and a first, in-frame reference having a known temperature;
acquiring an ambient temperature near said surface;
using the thermal image data for the first, in-frame reference and the surface portion to derive a calibrated surface temperature of the surface portion;
deriving the core body temperature of the subject using the calibrated thermal image data surface portion and ambient temperatures in a manner that accounts for a heat transfer impact of the ambient temperature upon the calibrated surface temperature; and
using the determined core body temperature to assess whether the subject may have a health condition.

26. The method of claim 25, wherein the health condition is selected from at least one of
a) SARS;
b) smallpox;
c) a health condition associated with bio-terrorism;
d) heat stroke;
e) hypothermia;
f) chronic wasting disease;
g) mad cow disease;
h) scrapies;
i) West Nile Virus; and
j) an avian disease.

27. The method of claim 25, wherein the health condition is smallpox.

28. The method of claim 25, wherein the health condition is associated with bio-terrorism.

29. The method of claim 25, wherein the health condition is selected from heat-stroke and hypothermia.

30. The method of claim 25, wherein the health condition is selected from chronic wasting disease, mad cow disease, and scrapies.

31. The method of claim 25, wherein the health condition is an avian disease.

32. The method of claim 31, wherein the avian disease is West Nile Virus.

* * * * *

UNITED STATES PATENT AND TRADEMARK OFFICE
CERTIFICATE OF CORRECTION

PATENT NO. : 7,340,293 B2 Page 1 of 1
APPLICATION NO. : 10/854574
DATED : March 4, 2008
INVENTOR(S) : McQuilkin It is certified that error appears in the above-identified patent and that said Letters Patent is hereby corrected as shown below:

On the title page item (56), under "U.S. PATENT DOCUMENTS" please add:
    6,292,685        9/2001            Pompei Signed and Sealed this Fifth Day of August, 2008

JON W. DUDAS
*Director of the United States Patent and Trademark Office*